United States Patent [19]

Mowry

[11] Patent Number: 4,677,235
[45] Date of Patent: Jun. 30, 1987

[54] PRODUCTION OF AROMATIC HYDROCARBONS FROM NATURAL GAS

[75] Inventor: John R. Mowry, Des Plaines, Ill.

[73] Assignee: UOP Inc., Des Plaines, Ill.

[21] Appl. No.: 837,480

[22] Filed: Mar. 7, 1986

[51] Int. Cl.[4] .......................... C07C 12/02; C07C 2/52
[52] U.S. Cl. ...................................... 585/415; 585/417
[58] Field of Search ................................ 585/415, 417

[56] References Cited

U.S. PATENT DOCUMENTS

| | | | |
|---|---|---|---|
| 2,992,283 | 7/1961 | Eng | 260/673 |
| 3,393,527 | 7/1968 | Swenson et al. | 62/16 |
| 3,761,389 | 9/1973 | Rollman | 208/64 |
| 3,791,157 | 2/1974 | Tracy et al. | 62/41 |
| 4,004,430 | 1/1977 | Solomon et al. | 62/18 |
| 4,070,165 | 1/1978 | Colton | 55/30 |
| 4,157,356 | 6/1979 | Bulford et al. | 585/415 |
| 4,180,689 | 12/1979 | Davies et al. | 585/407 |
| 4,329,532 | 5/1982 | Conn et al. | 585/407 |
| 4,347,394 | 8/1982 | Detz et al. | 585/419 |
| 4,451,685 | 5/1984 | Nevitt et al. | 585/415 |
| 4,528,412 | 7/1985 | Steacy | 585/415 |

OTHER PUBLICATIONS

Csicsery, Sigmund M., "Dehydrocyclodimerization" *Ind. Eng. Chem. Process Des. Dev., vol. 18, No. 2, 1979, pp. 191–197.*

*Primary Examiner*—Curtis R. Davis
*Attorney, Agent, or Firm*—Thomas K. McBride; John F. Spears, Jr.

[57] ABSTRACT

A process is disclosed for the conversion of at least a portion of the light hydrocarbons, such as propane, present in a natural gas feed stream into $C_6$-plus hydrocarbons including benzene. Noncondensibles such as hydrogen and nitrogen are separated from both the natural gas feed stream and from a reaction zone effluent stream in a common vapor-liquid separation vessel. The liquid stream produced in this initial separation is subjected to fractional distillation which recovers the $C_6$-plus product hydrocarbons and a stream of lighter hydrocarbons, which is passed into a dehydrocyclodimerization reaction zone.

10 Claims, 1 Drawing Figure

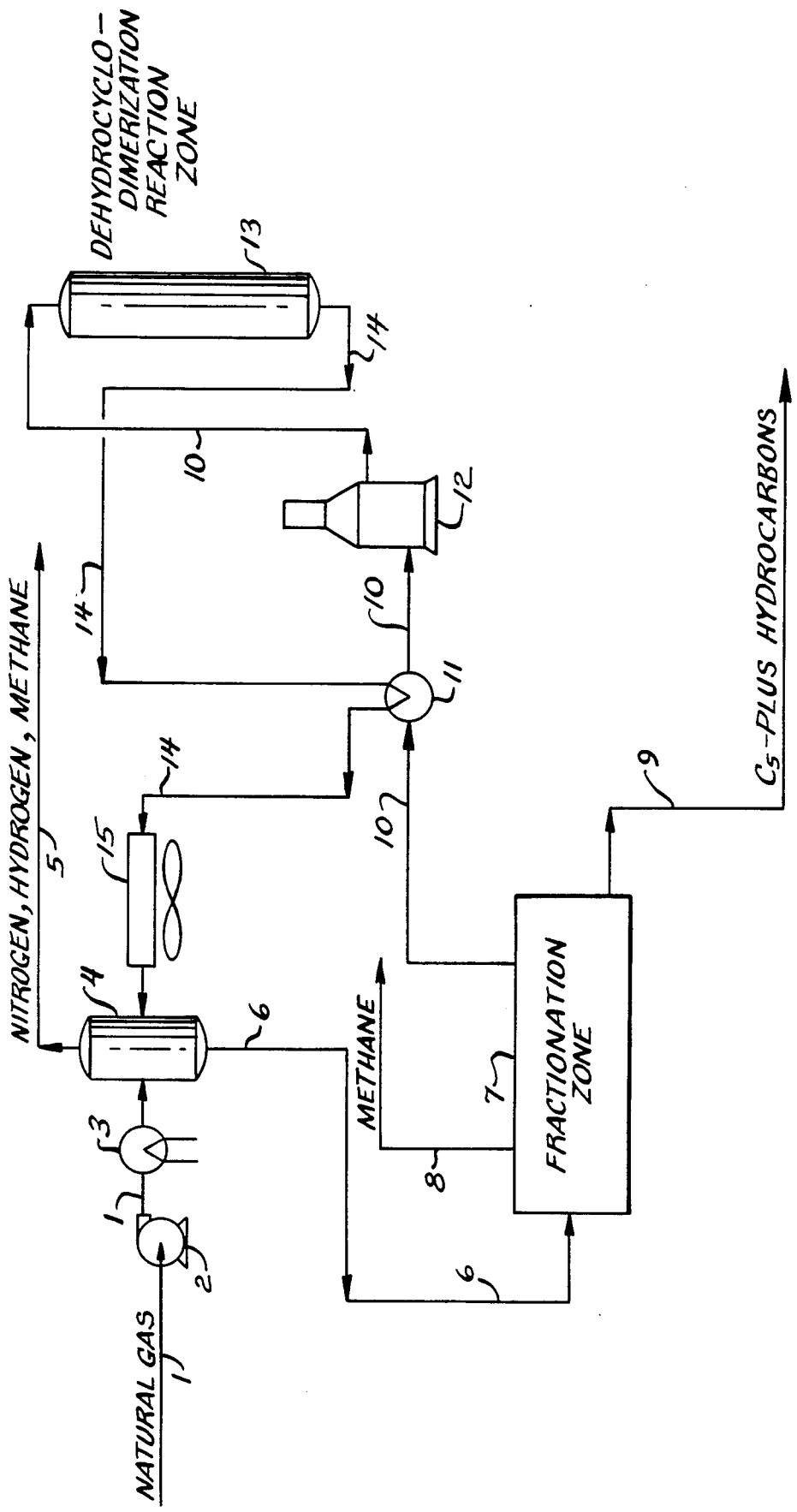

PRODUCTION OF AROMATIC HYDROCARBONS FROM NATURAL GAS

FIELD OF THE INVENTION

The subject process relates to a hydrocarbon conversion process. Specifically, the subject process relates to a process for the conversion of a light aliphatic hydrocarbon, such as propane or butane to benzene or other aromatic hydrocarbons. In a catalytic conversion zone the light aliphatic hydrocarbons are converted to aromatic hydrocarbons by a dehydrocyclodimerization reaction, with hydrogen also being produced. The resulting aromatic hydrocarbons are then passed into a fractional distillation complex utilized as a natural gas separation plant. This plant produces the reaction zone feedstream and recovers the reaction zone products. The invention therefore also relates to the design and operation of facilities employed to recover condensible hydrocarbons from natural gas feedstreams.

INFORMATION DISCLOSURE

There are a large number of references which describe the conversion of light aliphatic hydrocarbons to aromatic hydrocarbons. For instance, U.S. Pat. No. 2,992,283 issued to J. Eng describes the conversion of propylene to a variety of higher molecular weight saturated and unsaturated hydrocarbons including aromatics using a treated crystalline aluminosilicate as the catalyst. U.S. Pat. No. 4,347,394 issued to C. M. Detz et al describes the conversion of $C_5$-plus hydrocarbons to aromatics using a nonacidic zeolite supporting a platinum compound. U.S. Pat. No. 4,451,685 presents a process for conversion of ethylene and/or propylene to gasoline blending stocks over a crystalline borosilicate catalyst containing specific metals. U.S. Pat. No. 4,329,532 issued to P. J. Conn et al describes the conversion of $C_4$-minus olefins or mixtures of olefins and paraffins to aromatic hydrocarbons using a catalyst which comprises a crystalline silicate having a specified composition, crystallite size range, and X-ray diffraction pattern.

A review of dehydrocyclodimerization was published at page 191 of Volume 18, No. 2 (1979) of *Industrial and Engineering Chemistry—Process Design and Development* by S. M. Csicery. U.S. Pat. No. 4,180,689 issued to E. E. Davies et al describes the conversion of $C_3$-$C_8$ aliphatic hydrocarbons to aromatic hydrocarbons in a process which employs a catalyst comprising gallium supported on an aluminosilicate. U.S. Pat. No. 4,157,356 provides similar teaching for a gallium on silica catalyst. U.S. Pat. No. 3,761,389 issued to L. D. Rollman et al describes an improved process for converting $C_2$ to 400° Fahrenheit hydrocarbons to aromatics over a ZSM-5 type catalyst.

U.S. Pat. No. 4,528,412 issued to P. C. Steacy is pertinent for its description of a product recovery method for dehydrocyclodimerization processes.

Much development has occurred in the art of natural gas processing. There has therefore been established a wealth of literature describing the separation of natural gas into its numerous components. The various process schemes developed are tailored to the composition of the gas to accommodate such variation as the presence of high concentrations of nitrogen or methane. The known recovery processes employ many of the common processing techniques including partial condensation by indirect heat exchange, autorefrigeration by the steps of compression, cooling and expansion, and fractional distillation. U.S. Pat. Nos. 3,393,527 issued to L. K. Swenson et al.; 3,791,157 issued to R. R. Tracy et al.; 4,004,430 issued to S. M. Solomon et al. and 4,070,165 issued to J. W. Colton are believed pertinent for their showing of the use of these techniques to separate a natural gas stream and for their description of the fractionation of hydrocarbons from a natural gas stream.

BRIEF SUMMARY OF THE INVENTION

The invention is a unique process for the production of benzene from a natural gas feed stream comprising light aliphatic hydrocarbons such as a mixture of propane and butane. One of the novel features of the subject invention is the integration of a catalytic dehydrocyclodimerization reaction zone with a natural gas separation or gas liquids plant. The facilities used to separate "condensate" from the natural gas are thereby simultaneously employed to recover the $C_6$-plus products of the reaction zone and to recycle unconverted propane or butane. This dual usage of the recovery facilities can provide significant economic efficiencies when employing revamped or new gas separation plants.

A broad embodiment of the invention may be characterized as a hydrocarbon conversion process which comprises the steps of passing a hereinafter characterized reaction zone effluent stream comprising hydrogen, propane and $C_6$-plus hydrocarbons into a separation zone; passing a natural gas feed stream comprising methane, ethane and propane into the separation zone; withdrawing from the separation zone a separation zone off-gas stream comprising hydrogen and a first process stream comprising ethane, propane and $C_6$-plus hydrocarbons; passing the first process stream into a fractionation zone and therein separating the first process stream into at least a second process stream, which comprises propane, and a first product stream, which comprises $C_6$-plus hydrocarbons and is withdrawn from the process; and, passing the second process stream into a dehydrocyclodimerization reaction zone maintained at dehydrocyclodimerization conditions, and producing the previously referred to reaction zone effluent stream.

BRIEF DESCRIPTION OF THE DRAWING

The Drawing is a simplified process flow diagram illustrating several embodiments of the invention. In the basic flow of the process, propane present in natural gas entering through line 1 is converted to a mixture of $C_6$-plus aromatic hydrocarbons and hydrogen in the dehydrocyclodimerization reaction zone 13. The natural feed stream and reactor effluent of line 14 both flow into the vapor-liquid separator 4.

DETAILED DESCRIPTION

Dehydrocyclodimerization processes have been developed for the conversion of light aliphatic hydrocarbons to aromatic or nonaromatic $C_6^+$ hydrocarbons. The basic utility of these processes is the ability to convert low value, highly available $C_3$ and/or $C_4$ hydrocarbons into more valuable aromatic hydrocarbons and hydrogen. The process may therefore be performed simply to upgrade the value of the hydrocarbons. It may also be desired to correct an overabundance of $C_3$ and $C_4$ hydrocarbons or to fulfill a need for the aromatic hydrocarbons. The aromatic hydrocarbons are highly useful in the production of a wide range of petrochemicals, with benzene being one of the most widely used basic feed hydrocarbon chemicals. It is an objective of the subject invention to provide a process for the conversion of light aliphatic hydrocarbons in natural gas to $C_6$-plus hydrocarbons. It is a further objective of the subject invention to provide a more economical dehydrocyclodimerization process for the conversion of light aliphatic hydrocarbons into benzene.

The subject process achieves these objectives by employing the unique integration of a natural gas separation plant with a dehydrocyclodimerization reaction zone. A natural gas plant must normally be designed to accommodate a variety of materials having an extreme boiling point range similar to that of the dehydrocyclodimerization reaction zone. Existing or new gas concentration plants may therefore be adaptable to the subject process and function as the relatively expensive product recovery section of the dehydrocyclodimerization zone. This greatly reduces the capital cost of a dehydrocyclodimerization zone. In addition the gas separation zone will also function as the feed preparation zone producing the original charge stock to the process. The gas plant also recovers unconverted $C_2$-$C_4$ paraffins for recycling to the reaction zone.

In the subject process the feed aliphatic hydrocarbons recovered from a natural gas feed stream are passed into a dehydrocyclodimerization zone which converts a significant portion of the entering hydrocarbons into aromatic hydrocarbons. The term "reaction zone" is intended to indicate the totality of the equipment employed in the conversion step wherein the feed hydrocarbons are passed through a reaction chamber(s), which may contain several beds of catalyst, and interstage heaters, etc. The composition of the efffluent stream of the dehydrocyclodimerization zone will depend upon such factors as the composition of the feedstock. The presence of olefinic hydrocarbons within the feedstream would tend to cause the production of branch chain or acyclic $C_6+$ hydrocarbons. However, few olefinic hydrocarbons are normally present in natural gas. When processing a feedstream comprising propane or butane or mixtures thereof, the reaction zone effluent stream will contain benzene, toluene, ethylbenzene, a mixture of the various xylenes, styrene, N-propyl benzene, cumene, methylethyl benzene, trimethyl benzenes, methyl propyl benzenes, dimethylethyl benzenes, indane, $C_{11}$ alkylbenzenes, naphthalene, methylnaphthalene, dimethylnaphthalene and a very small amount of heavier aromatic compounds. When processing a feedstream of relatively pure propane and/or butane, the $C_6+$ liquid product composition should contain less than 0.1 weight percent of nonaromatics.

The feed compounds to the dehydrocyclodimerization zone are light aliphatic hydrocarbons having from 2 to 4 carbon atoms per molecule. Feed streams may comprise a single compound or a mixture of two or more of these compounds. The preferred feed compounds for the subject process are propane and the butanes. It is preferred that over 50 mole percent of the feed hydrocarbons have three or more carbon atoms per molecule. Some butylenes and propylenes may be present in the feed stream. The feed stream to the process may also contain some $C_2$ and $C_5$ hydrocarbons. It is preferred that the concentration of $C_5$ hydrocarbons in the feed stream to the subject dehydrocyclodimerization process is held to a reduced level less than 10 mole percent.

The configuration of the dehydrocyclodimerization reaction zone and the composition of the catalyst employed within the reaction zone are not basic elements of the invention or limiting characteristics of the invention. Nevertheless, in order to provide a background to the subject invention, it is felt useful to describe the preferred reactor system for use in the invention. This system comprises a moving bed radial flow multi-stage reactor such as is described in U.S. Pat. Nos. 3,652,231; 3,692,496; 3,706,536; 3,785,963; 3,825,116; 3,839,196; 3,839,197; 3,854,887; 3,856,662; 3,918,930; 3,981,824; 4,094,814; 4,110,081; and 4,403,909. These patents also describe catalyst regeneration systems and various aspects of moving catalyst bed operations and equipment. This reactor system has been widely employed commercially for the reforming of naphtha fractions. Its use has also been described for the dehydrogenation of light paraffins.

The preferred moving bed reactor system employs a spherical catalyst having a diameter between about 1/64 and ⅛ inch. The catalyst preferably comprises a support material and a metallic component deposited on the support material as through impregnation or coprecipitation. The previously cited references point out that the current trend is the use of a zeolitic support material, with the catalyst referred to in the art as a ZSM-5 type zeolite being often specified as a preferred material. When properly formulated, it appears this zeolitic material by itself has significant activity for the dehydrocyclodimerization reaction. Further information on such zeolitic catalysts for the DHCD reaction can be obtained from European patent application No. 83 20114229 by E.P. Kieffer. However, it is still preferred to employ a metallic component within the catalyst system to increase the activity of the catalyst. The preferred metallic component is gallium as described in the previously cited U.S. Pat. No. 4,180,689. The catalyst may contain from about 0.15 to 2.4 weight percent gallium which is preferably exchanged or impregnated into the zeolitic component of the catalyst rather than forming a portion of the original (as produced) zeolite. A preferred range of the gallium component is from 0.3 to 1.0 weight percent. Further information on catalysts and operating conditions for the DHCD zone may be obtained from U.S. Pat. No. 4,175,057 and from U.S. Pat. No. 4,565,897 which is incorporated herein by reference. It is also pertinent in this regard to note that this patent is specifically directed to a dehydrocyclodimerization process wherein the feedstream contains from between 10 to 50 weight percent ethane, thus allowing the conversion of substantial quantities of ethane present in the natural gas.

The zeolitic material, preferably ZSM-5, is normally bound during the particle forming stage with another material primarily to increase the strength and durability of the catalyst. This binding material is often a form of clay or alumina. It is highly preferred that this binder comprises an alumina, as can be prepared by the gelation of a hydrosol precursor in accordance with the well-known oildropping method. For instance, an alumina hydrosol can be prepared by digesting aluminum in aqueous hydrochloric acid and/or aluminum chloride solution. The final composite can be formed in a variety of shapes or by oil-dropping and finished using conventional catalyst manufacturing techniques.

The dehydrocyclodimerization reaction zone is preferably operated at a temperature between about 920 degrees–1050 degrees Fahrenheit (487 degrees–565 degrees Celsius), a pressure under 100 psig (689 kPa g) and a liquid hourly space velocity of 0.5 to 6.0 hr$^{-1}$. Hydrogen-producing reactions are normally favored by lower pressures, and pressures under about 70 psig (483 kPa g) at the outlet of the reaction zone are highly preferred.

It is believed that those skilled in the art of petroleum and petrochemical process design may determine proper operating conditions, vessel designs, and operating procedures for the subject process through the use of standard process design techniques after having now been appraised of the overall flow of the process. The fractionation zone employed in the process preferably contains trayed fractionation columns having sieve-type trays and being of relatively standard design. Suitable fractionation zones may be readily designed by those skilled in the art. The operating conditions required in the fractionation zones are dependent upon the compounds being separated and the desired separation.

A more limited embodiment of the invention may accordingly be characterized as a process for upgrading hydrocarbons contained in natural gas, which process comprises the steps of passing a hereinafter characterized reaction zone effluent stream comprising hydrogen, ethane, propane and $C_6$-plus aromatic hydrocarbons into a vapor·liquid separation zone operated at conditions effective to separate entering chemicals into a vapor-phase off-gas stream comprising hydrogen and a liquid-phase first process stream comprising ethane, propane and $C_6$-plus aromatic hydrocarbons; passing a natural gas feed stream comprising methane, ethane, propane and butane into the vapor-liquid separation zone; passing the first process stream into a second separation zone operated at conditions effective to separate entering hydrocarbons of the first process stream into at least a second process stream, which comprises propane, and a first product stream, which product stream comprises $C_6$-plus hydrocarbons and is withdrawn from the process; and, passing the second process stream into a dehydrocyclodimerization reaction zone operated at dehydrocyclodimerization conditions and producing the previously referred to reaction zone effluent stream.

The illustration of the flow of the subject process presented in the drawing has been simplified by not illustrating many required pieces of conventional equipment which are not pertinent or necessary to a discussion of the subject invention. These engineering features include control systems, pumps and compressors, reactor and fractionation column internals, overhead condensing systems and reboiling systems for the fraction ation columns and similar process equipment of a generalized nature.

Referring now to the drawing, a natural gas feed stream enters the overall process through line 1. Preferably, this natural gas feed stream has been treated in suitable facilites for the removal of water, hydrogen sulfide and other sulfur compounds such as carbonyl sulfide. The natural gas feed stream is first compressed in the compressing means 2 if this pressurization step is required. The natural gas feed stream is then passed through a cooling means represented by the indirect heat exchange means 3 to effect a partial condensation of the natural gas. There will thereby be formed a mixed phase stream which will comprise methane, nitrogen, ethane, propane, butane and small amounts of heavier hydrocarbons including $C_5$ and $C_6+$ acyclic hydrocarbons. This mixed phase stream is passed through line 1 into a vapor-liquid separation vessel 4. Also passed into the separation vessel 4 is a mixed phase reactor zone effluent stream from line 14. The reaction zone effluent stream comprises hydrogen, ethane, propane, butane and $C_6+$ aromatic hydrocarbons including benzene, toluene and xylenes.

The vapor-liquid separation zone 4 is operated at conditions which result in the separation of the entering chemicals into an off-gas stream discharged through line 5 which comprises the relatively noncondensible nitrogen and hydrogen and normally at least some portion of methane which enters the vapor-liquid separation zone. Under extreme conditions of cooling all of the methane could be condensed and removed as a liquid from the separation zone. However this is not the preferred mode of operation. The off-gas stream of line 5 will also contain an equilibrium concentration of the other components which enter the separation zone including ethane, propane and butane. The concentration of these hydrocarbons is preferably quite minimal. The gas stream of line 5 may be discharged to the appropriate recovery facilities or may be utilized as fuel due to its hydrogen and methane content. The off-gas stream of line 5 may also be combined with methane and ethane discharged from other portions of the overall process or with any unprocessed natural gas to form a natural gas product stream.

A stream of the liquid phase materials which are collected in the lower portion of the vapor-liquid separation vessel 4 are withdrawn through process line 6. This stream will comprise propane, butane, and $C_5$ and $C_6$ hydrocarbons including the benzene, toluene and xylene produced in the dehydrocyclodimerization reaction zone, and an equilibrium concentration of the more volatile materials present in the separation zone. This liquid phase stream will therefore contain some finite quantity of hydrogen and methane in addition to a variable and probably significant amount of ethane. The liquid phase process stream of line 6 is passed into a fractionation zone 7. Fractional distillation is the preferred method of performing the separation of the various components of the stream of line 6, although other separatory methods could be used in addition to or to the exclusion of fractional distillation within the overall zone 7 which may be more properly referred to as a second separation zone. Nevertheless, the entering materials are preferably separated into a light gas stream comprising methane discharged through line 8, a heavy hydrocarbon product stream comprising $C_5+$ hydrocarbons discharged through line 9 and a second process stream comprising those hydrocarbons, which it is desired to charge to the dehydrocyclodimerization reaction zone, carried by line 10. The normally gaseous stream carried by line 8 is expected to contain the hydrogen or nitrogen dissolved in the liquid phase stream carried by line 6 and perhaps some ethane in addition to the methane. The amount of ethane being discharged through line 8 will in most instances be determined by the desired concentration of ethane in the materials flowing through line 10. The split between the presence of $C_5$ hydrocarbons in the process streams of lines 9 and 10 need not be exact since it is acceptable to charge $C_5$ hydrocarbons to the dehydrocyclodimerization reaction zone. The lack of any requirement for a precise separation of the various hydrocarbons within the fractionation zone allows the utilization of lower cost fractionation equipment and/or the operation of the fractionation columns in a mode which reduces the utility costs of operation as by minimizing reflux and stripping requirements.

The hydrocarbon stream of line 10 is first heated by indirect heat exchange in the heat exchanger 11. It is then passed into a fired heater 12 which raises the temperature of the materials in line 10 to the desired inlet temperature of the downstream dehydrocyclodimerization reaction zone. The thus heated hydrocarbons will flow into the reaction zone 13 wherein they are contacted with beds of dehydrocyclodimerization catalyst at suitable operating conditions. Preferably, a multi-stage moving bed operating system as described herein is employed as the reaction zone. This system utilizes at least three reactors in sequence with inter-stage heating to replace the heat of reaction of the highly endothermic reaction.

There is thus produced a vapor phase reaction zone effluent stream carried by line 14 which will comprise an admixture of the unconverted charge materials including ethane, propane and butane and the product materials of the reaction including hydrogen, benzene, toluene, xylenes and other $C_8+$ aromatic hydrocarbons. The catalyzed dehydrocyclodimerization reaction is highly selective to the production of aromatic hydrocarbons when processing a totally paraffinic feed stream. A minor amount, less than 2 mole percent, of $C_6$-plus acyclic hydrocarbons may be produced during the dehydrocyclodimerization reaction. If for some reason there is any appreciable percentage of olefinic hydrocarbons in the feed stream, the proportion of acyclic hydrocarbons produced will increase. The reaction zone effluent stream is then cooled by indirect heat exchange in the means 11 against the feed stream. It is then further cooled and preferably partially condensed by indirect heat exchange as through the use of the air cooled indirect heat exchange means 15. The effluent stream of the reaction zone is then passed into the vapor-liquid separation vessel 4. The separation vessel is preferably operated at a pressure above 400 psig (2,758 k Pag). It will then be necessary to compress the reaction zone effluent stream. This may be done after cooling and partial condensation to allow the usage of low pressure exchangers and to obtain some economies attributable to pressurizing the liquid-phase condensate rather than vapor. Those skilled in the art will recognize that the embodiment illustrated in the drawing is subject to appreciable variation beyond that already discussed. For instance, a single fixed bed of catalyst could be employed as the reaction zone. Various alternative heat exchange methods could be employed to cool or heat both the feed and effluent streams of the reaction zone. In addition, autorefrigeration type processing techniques could be employed to partially or totally separate the effluent of the reaction zone either prior to or in conjunction with the separation vessel 4. Pressure swing separation or the use of selective membranes, such as for hydrogen separation from the gases, may also be employed to separate the effluent of the reaction zone. It is also contemplated that a significant variation is possible in the structure and orientation of the fractionation zone 7. The preferred structure of the fractionation zone is a series or "train" of fractionation columns. Therefore in a first fractionation column the entering hydrocarbons would be separated into a net overhead stream of methane and some ethane. The net bottoms of the first fractionation column is then passed into a second fractionation column which produces a net overhead stream comprising some ethane and essentially all of the propane and butane which enters the second fractionation column. The net bottoms stream of the second fractionation column would be discharged from the fractionation zone as the stream of line 9. The overhead stream of the second fractionation column would comprise the stream 10. Three or more fractionation columns could be employed if it is perhaps desired to discharge relatively high-purity streams of one or more of the components of the entering gases such as a relatively high-purity stream of methane or butane. In addition, the sequence of operation of the fractionation columns could be changed such that the $C_5+$ or $C_6+$ net products stream of line 9 could be removed as the bottoms stream of a first fractionation column with the overhead vapor of the first fractionation column being transferred to subsequent fractionation columns. Yet another variation in the structure and operation of the fractionation zone would comprise the utilization of a single fractionation column designed to produce the feed stream to the dehydrocyclodimerization zone as a sidecut stream which could be stripped if so desired. It is also contemplated that an absorption-stripping sequence in which a gas stream is passed upward countercurrent to descending absorption liquid and the liquid is subsequently stripped in a fractionation column could be employed within either the first separation zone or the fractionation zone.

The relative distribution of the products produced in the subject process will be dependent upon several factors including the compostion of the feedstream, the effectiveness of the DHCD catalyst and the operating conditions employed within the DHCD reaction zone and the fractionation schemes employed within the process flow.

In one embodiment of the invention all or a portion of the $C_2$-plus light ends produced in the reaction zone are recycled to the reaction zone for the production of additional quantities of aromatic hydrocarbons. The product distribution would change depending upon the amount of recycling and the amount of conversion of these light hydrocarbons achieved in the DHCD reaction zone. It is presently not preferred to pass methane into the DHCD reaction zone. Therefore, it is preferred to separate methane to the extent economically feasible from any feed or recycled gases.

This separation can be performed in a number of different ways including pressure swing adsorption, partial condensation through the use of low temperatures in a cryogenic separation system similar to the "cold boxes" employed for gas recovery and separation, or through the use of membranes which selectively allow the passage of one or more hydrocarbons. The use of a low temperature separation technique is preferred. In this technique, the gases to be recycled would preferably be compressed, cooled and then flashed to generate low temperature fluids which would be used to achieve the condensation of ethane. Reference may be made to U.S. Pat. No. 4,528,412, which is incorporated herein by reference, and illustrates a low temperature gas separation technique suitable for separating light gases. In this reference, a bottom stream from a stripping column contains propane and butane recovered by this technique in addition to a variable amount of ethane, with this bottom stream being suitable for recycling to the DHCD reaction zone of the process described therein. The use of pressure swing adsorption in the separation of the gases produced in a DHCD reaction zone is described in U.S. Pat. No. 4,547,205.

As previously indicated, it is preferred that the natural gas feed stream is treated for the removal of sulfur compound and for the removal of any significant amounts of water. Such feed pretreatment steps may not be required if the natural gas stream is already in a sweet and dry state or if the catalyst or processing steps do not require such pretreatment. Preferably, the gas treatment would comprise the countercurrent contacting of the gas stream with an amine as an aqueous solution, with monoethanol amine or diethanol amine being employed. This pretreatment step will also effect the removal of carbon dioxide from the natural gas feed stream. Diglycol amine could also be employed if so desired. It is preferred that the feed pretreatment step removes hydrogen sulfide down to a level of less than 50 ppm. The initial separation of the natural gas feed stream by partial condensation may also result in some reduction in the concentration of $CO_2$ and $H_2S$ in the material being charged to the reaction zone. It is also preferred to remove water from the feed stream since the preferred zeolitic type catalysts may be adversely affected by the presence of significant concentrations of water in the reaction zone. It may also be desirable to remove water to prevent the formation of hydrates in transmission lines or to meet water dew point requirements or to prevent the solidification of water in various process lines which operate at low temperature. In general, it would be preferred to dry the gas down to a dew point of about $-20$ degrees Fahrenheit ($-29$ degrees Celsius). It is preferred to utilize a glycol type drying system. Most commonly used glycols are triethylene glycol, diethylene glycol and ethylene glycol. Basic drying steps include the countercurrent contacting of the gas stream with a descending stream of the glycol solution, with the glycol then being heated and passed into a regenerator operated at a elevated temperature. Solid desiccants could also be employed for the drying of the feed gas stream, with solid dessicants being able to reduce the water content of the gas to less than 1 ppm. When low levels of water content are required, it is a normal practice to utilize at least two drying zones in sequence with the first being a glycol type drying zone and the second being a desiccant type drying zone. Activated alumina, silica gel, silica alumina beads and molecular sieves such as a type 4A sieve are suitable materials as desiccants. Further information on the sweetening and drying of the natural gas feed stream as well as the separation of various components of a natural gas stream may be obtained by reference to previously cited U.S. Pat. No. 4,070,165, which is hereby incorporated herein by reference.

What is claimed is:

1. A hydrocarbon conversion process which comprises the steps of:
    (a) compressing and passing a hereinafter characterized reaction zone effluent stream comprising hydrogen, propane and $C_6$-plus hydrocarbons into a separation zone operated at a pressure in excess of 400 psig;
    (b) passing a natural gas feed stream comprising nitrogen, methane, ethane and propane into the separation zone;
    (c) withdrawing from the separation zone a separation zone off-gas stream comprising nitrogen and hydrogen and a first process stream comprising ethane, propane and $C_6$-plus hydrocarbons;
    (d) passing the first process stream into a fractionation zone and therein separating the first process stream into at least a second process stream, which comprises propane, and a first product stream, which comprises $C_6$-plus hydrocarbons and is withdrawn from the process; and,
    (e) passing the second process stream into a dehydrocyclodimerization reaction zone maintained at dehydrocyclodimerization conditions including a pressure under 100 psig, and producing the previously referred to reaction zone effluent stream.

2. The process of claim 1 wherein the separation zone off-gas stream comprises methane.

3. The process of claim 2 further limited in that a third process stream comprising methane is produced in the fractionation zone and discharged from the process.

4. The process of claim 1 further characterized in that a bed of a catalyst comprising gallium is present within the reaction zone.

5. A process for upgrading hydrocarbons contained in natural gas, which process comprises the steps of:
    (a) compressing and passing a hereinafter characterized reaction zone effluent stream comprising hydrogen, ethane, propane and $C_6$-plus aromatic hydrocarbons into a vapor-liquid separation zone operated at conditions, including a pressure in excess of 400 psig, effective to separate entering chemicals into a vapor-phase off-gas stream comprising hydrogen and nitrogen and a liquid-phase first process stream comprising ethane, propane and $C_6$-plus aromatic hydrocarbons;
    (b) passing a natural gas feed stream comprising nitrogen, methane, ethane, propane and butane into the vapor-liquid separation zone;
    (c) passing the first process stream into a second separation zone operated at conditions effective to separate entering hydrocarbons of the first process stream into at least a second process stream, which comprises propane, and a first product stream, which product stream comprises $C_6$-plus hydrocarbons and is withdrawn from the process; and,
    (d) passing the second process stream into a dehydrocyclodimerization reaction zone operated at dehydrocyclodimerization conditions which include a pressure under 100 psig and producing the previously referred to reaction zone effluent stream.

6. The process of claim 5 further characterized in that the vapor-phase off-gas stream comprises methane.

7. The process of claim 6 further characterized in that a third process stream comprising methane is produced in the second separation zone and is discharged from the process.

8. The process of claim 6 further characterized in that the second separation zone comprises at least one fractionation column.

9. The process of claim 8 further characterized in that a bed of dehydrocyclodimerization catalyst comprising gallium is present within the reaction zone.

10. The process of claim 8 further characterized in that the natural gas feed stream comprises $C_6$ hydrocarbons.

* * * * *